United States Patent [19]
Helene et al.

[11] Patent Number: 6,133,024
[45] Date of Patent: Oct. 17, 2000

[54] GENE EXPRESSION CONTROL

[75] Inventors: Claude Helene; Carine Giovannangeli, both of Paris, France

[73] Assignee: Aventis Pharma S.A., Antony, France

[21] Appl. No.: 09/074,357

[22] Filed: May 7, 1998

Related U.S. Application Data

[63] Continuation of application No. 08/669,274, filed as application No. PCT/FR94/01536, Dec. 27, 1994, abandoned.

[30] Foreign Application Priority Data

Dec. 29, 1993 [FR] France ................................. 93 15798

[51] Int. Cl.$^7$ ............................ C07H 21/04; C07H 21/02
[52] U.S. Cl. .................... 435/320.1; 536/23.1; 536/24.1; 536/24.5
[58] Field of Search ............................ 435/172.3, 320.1, 435/375; 536/23.1, 24.5, 24.1; 514/44

[56] References Cited

U.S. PATENT DOCUMENTS

| | | | |
|---|---|---|---|
| 5,624,803 | 4/1997 | Noonberg et al. | 436/6 |
| 5,700,657 | 12/1997 | Beaudry et al. | 435/69.5 |

FOREIGN PATENT DOCUMENTS

| | | |
|---|---|---|
| 2 687 411 | 8/1993 | France . |
| WO 91/06626 | 5/1991 | WIPO . |
| WO 92/19732 | 11/1992 | WIPO . |
| WO 93/12230 | 6/1993 | WIPO . |

OTHER PUBLICATIONS

Branch et al. "A Good Antisense is Hard to Find" TIBS vol. 23:45–50, Feb. 1998.

Stull et al. "Antigene, Ribozyme and Aptamer Nucleic Acid Drugs: Progress and Prospects" Pharmaceutical Research vol. 12(4):465–483, 1995.

Orkin et al. "Report and Recommendations of the Panel to Assess the NIH Investment in Research on Gene Therapy", Dec. 7, 1995.

Giovannangeli et al., Oligonucleaotide clamps arrest DNA synthesis on a single–stranded DNA target, Proc. Natl. Acad. Sci., USA, 90, 10013–10017 (1993).

Giovannangeli et al., Single–Stranded DNA as a Target for Triple–Helix Formation, J. Am. Chem. Soc., 113, 7775–7777 (1991).

Helene, The anti–gene strategy: control of gene expression by triple–forming–oligonucleotides, Anti–Cancer Drug Design 6, 569–584 (1991).

James, Towards gene–inhibition therapy: a review of progress and prospects in the field of antiviral antisense nucleic acids and ribozymes, Antiviral Chemistry & Chemotherapy 2(4), 191–214 (1991).

*Primary Examiner*—Robert A. Schwartzman
*Assistant Examiner*—Sean McGarry
*Attorney, Agent, or Firm*—Finnegan, Henderson, Farabow, Garrett & Dunner, L.L.P.

[57] ABSTRACT

The present invention relates to new vectors, pharmaceutical compositions containing them, and their therapeutical uses. More particularly, it relates to new molecules capable of acting, in a very selective and efficacious way, on the expression of genes.

20 Claims, 2 Drawing Sheets

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:1:

CCACTTTTTA AAAGAAAAGG GGGGACTGG                                              29

(2) INFORMATION FOR SEQ ID NO:2:

(i) SEQUENCE CHARACTERISTICS:
        (A) LENGTH: 39 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:2:

TTTTCTTTTC CCCCCTTTTT TTCCCCCCTT TTCTTTTAA                                   39

(2) INFORMATION FOR SEQ ID NO:3:

(i) SEQUENCE CHARACTERISTICS:
        (A) LENGTH: 38 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:3:

TTTTCTTTTC CCCCCTTTTT TCCCCCCTTT TCTTTTAA                                    38

(2) INFORMATION FOR SEQ ID NO:4:

(i) SEQUENCE CHARACTERISTICS:
        (A) LENGTH: 38 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:4:

TTTTCTTTTC CCCCCTTTTG TCCCCCCTTT TCTTTTAA                                    38

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:5:

```
TTTCCCCCCT TCTGTCCCCC CTTTT                                              25

(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:6:

TTTGGGGGGT TCTGTCCCCC CTTTT                                              25

(2) INFORMATION FOR SEQ ID NO:7:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:7:

TTTTCTTTTC CCCCCTTCTG TCCCCCCTTT TCTTTT                                  36

(2) INFORMATION FOR SEQ ID NO:8:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:8:

TTTTCTTTTG GGGGGTTCTG TCCCCCCTTT TCTTTT                                  36

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:9:

GCTAGAAGGA GAGAGATGGG                                                    20

(2) INFORMATION FOR SEQ ID NO:10:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:10:

TCTTCCTCTC TCTTATTTCT CTCTCCTTCT TTT                                     33
```

-continued

```
(2) INFORMATION FOR SEQ ID NO:11:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:11:

TGTTGGTGTG TGTTATTTCT CTCTCCTTCT TTT                                33

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:12:

GCCAGGGGGA AAGAAAAAAT AT                                            22

(2) INFORMATION FOR SEQ ID NO:13:

(i) SEQUENCE CHARACTERISTICS:
        (A) LENGTH: 39 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:13:

TCCCCCTTTC TTTTTTCTCC TTTTTTCTTT CCCCCTTTT                          39

(2) INFORMATION FOR SEQ ID NO:14:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:14:

TCCCCCTTTC TTTCTCCTTT CTTTCCCCCT TTT                                33

(2) INFORMATION FOR SEQ ID NO:15:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:15:

TGGGGGTTTG TTTCTCCTTT CTTTCCCCCT TTT                                33

(2) INFORMATION FOR SEQ ID NO:16:

(i) SEQUENCE CHARACTERISTICS:
        (A) LENGTH: 23 base pairs
```

```
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:16:

AGAAGAGGGA GAGAGAGAGA AGG                                               23

(2) INFORMATION FOR SEQ ID NO:17:

(i) SEQUENCE CHARACTERISTICS:
            (A) LENGTH: 50 base pairs
            (B) TYPE: nucleic acid
            (C) STRANDEDNESS: double
            (D) TOPOLOGY: linear (ii) MOLECULE TYPE: other nucleic acid (xi) SEQUENCE DESCRIPTION: SEQ ID NO:17:

TCTTCTCCCT CTCTCTCTCT TCCTCCGCCT TCTCTCTCTC TCCCTCTTCT                  50
```

GENE EXPRESSION CONTROL

This application is a continuation of U.S. application Ser. No. 08/669,274, filed Jun. 28, 1996, now abandoned, which is a 371 of PCT/FR94/01536, filed Dec. 27, 1994.

The present invention relates to new vectors, to pharmaceutical compositions containing them and to their uses in therapy. More particularly, it relates to new vectors making it possible to affect, highly selectively and very efficiently, the expression of genes.

The control of the expression of target genes by means of oligonucleotides constitutes a therapeutic approach which is undergoing increasing development. This approach is based on the ability of oligonucleotides to hybridize specifically with complementary regions of a nucleic acid and thus to inhibit specifically the expression of determined genes. This inhibition can intervene either at the translational level (antisense oligonucleotide) or at the transcriptional level (anti-gene oligonucleotide).

Antisense oligonucleotides are nucleic sequences capable of hybridizing selectively with target cell messenger RNAs so to inhibit their translation into protein. With the target mRNA, these oligonucleotides form locally double stranded regions of RNA/mRNA or even DNA/mRNA type, by conventional interaction of Watson-Crick type. This may involve, for example, small-sized synthetic oligonucleotides complementary to cell mRNAs, introduced into the target cells. Such oligonucleotides have, for example, been described in patent No. EP 92 574. It may also involve antisense genes whose expression in the target cell produces RNAs complementary to cell mRNAs. Such genes have been described, for example, in patent No. EP 140 308.

More recently, a new type of oligonucleotides capable of controlling the expression of target genes has been demonstrated. These oligonucleotides do not hybridize with cell mRNAs, but directly with the double stranded genomic DNA. This new approach is based on the demonstration that some oligonucleotides are capable of interacting specifically in the large groove of the DNA double helix to form triple helices locally, resulting in an inhibition of the transcription of target genes. These oligonucleotides recognize the DNA double helix selectively at the oligopurine.oligopyrimidine sequences, that is to say in the regions which have an oligopurine sequence on one strand and an oligopyrimidine sequence on the complementary strand, and form a triple helix locally there. The bases of the third strand (the oligonucleotide) form hydrogen bonds (Hoogsteen or reverse Hoogsteen bonds) with the purines of the Watson-Crick base pairs. The anti-gene oligonucleotides may contain the following bases:

thymidine (T), which is capable of forming triplets with the A.T doublets of the double stranded DNA (Rajagopal et al., Biochem. 28 (1989) 7859);

adenine (A), which is capable of forming triplets with the A.T doublets of the double stranded DNA;

guanine (G), which is capable-of forming triplets with the G.C doublets of the double stranded DNA;

protonated cytosine (C+), which is capable of forming triplets with the G.C doublets of the double stranded DNA (Rajagopal et al., op. cit.).

Anti-gene oligonucleotides have been described in particular by Hélène in Anti-Cancer drug design 6 (1991) 569.

The present invention describes a new approach for the control of the expression of target genes. It lies more particularly in the demonstration that it is possible to produce genetically in vivo therapeutic RNAs which are capable of forming triple helices with single-strand target nucleic acids. Preferentially, it lies in the genetic production in vivo of therapeutic RNAs capable of forming triple helices with ribonucleic targets.

The invention relates especially to the double stranded DNA sequences coding for such therapeutic RNAs. It also relates to the vectors usable for in-vivo production of these therapeutic RNAs especially in the context of a gene therapy. It also relates to the pharmaceutical compositions including these double stranded DNAs or these vectors.

Another aspect of the invention lies in a process for controlling the expression of cell genes by transformation of target cells by means of a vector such as the abovementioned.

More particularly, the present invention therefore relates to a double stranded DNA coding for an RNA capable of forming a triple helix with a single-strand target nucleic acid.

The double stranded DNAs of the invention code more particularly for composite PNAs including at least:

a first region capable of forming a double helix with the targeted single-strand nucleic acid or with a portion thereof, a second region capable of forming a triple helix with the double helix thus formed or with a portion of the latter, and one or two arms connecting the two regions, it being possible for each of the regions to be continuous or interrupted.

In a first particular embodiment of the invention the first region of the composite RNA forms a double helix with the targeted single-strand nucleic acid by conventional interaction of Watson-Crick type, and then the second region forms a triple helix by hydrogen bonds (of Hoogsteen or reverse Hoogsteen type) with this double helix or with a portion of the latter (see FIGS. 1–4).

Figure 5:
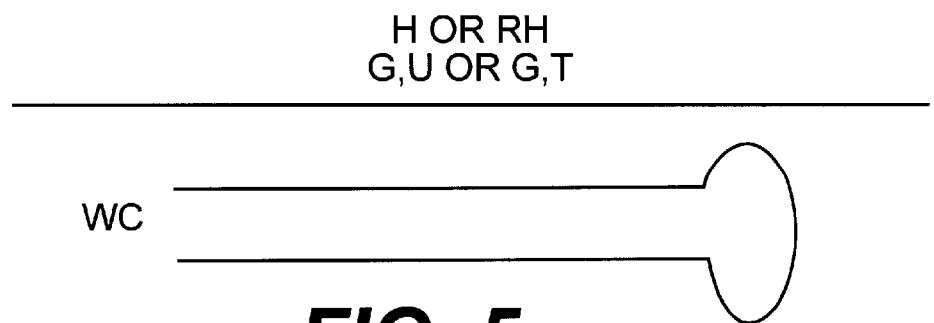
FIG. 5 depicts an embodiment of the triplex forming RNA oligonucleotides of the invention.

In another particular embodiment of the invention the two regions of the composite RNA of the invention form a double helix between them by coupling of Watson-Crick type, and this double helix interacts by hydrogen bonds (of Hoogsteen or reverse Hoogsteen type) with the targeted single-strand nucleic acid, thus forming a triple helix (see FIG. 5).

The single-strand targeted nucleic acid may be an RNA such as, for example, a messenger RNA (mRNA), a transfer RNA (tRNA), a ribosomal RNA (rRNA) or a viral RNA. It may equally be a single-strand DNA appearing, for example, during the replication of the double stranded DNA or of a DNA region which is locally open naturally.

The present invention is particularly suited to the control of the expression of viruses, especially viruses containing RNA or DNA as a single strand, at different stages of the viral cycle. Different single-strand nucleic acids can, in fact, constitute targets for the therapeutic RNAs of the invention, and especially viral RNA (in the case of viruses containing RNA, such as, for example, retroviruses, polioviruses, flu viruses, and the like). The action of the therapeutic RNAs of the invention on the RNA makes it possible to inhibit the reverse transcription, that is to say to act at an early stage of the viral cycle;

proviral (in the case of viruses containing RNA) or viral DNA. The therapeutic RNAs of the invention can act before or after an incorporation of the viral or proviral DNA into the genome of the infected cell. The interaction takes place after local opening of the DNA double helix, and the triple helices thus formed are much more stable than the conventional triple helices (involving an anti-gene oligonucleotide);

viral mRNA. The action of the therapeutic RNAs of the invention on the viral mRNAs makes it possible to inhibit the translation and the expression of viral proteins.

More particularly, the RNAs of the invention are capable of forming triple helices with the targeted single-strand nucleic acids in the regions preferably consisting of purine bases (A and G: polyPu region) or of pyrimidine bases (T/U. and C: polyPy region) or of T/U and G bases (polyT/U, G region).

Thus, when the targeted nucleic acid (or a specific region of the latter) is composed essentially of purine bases (polyPu), the therapeutic RNA of the invention may include a first region composed of complementary pyrimidine bases (Watson-Crick region), one or two oligonucleotide arms, and a second region (Hoogsteen region) composed of the bases U, C and/or G, which interact with the purine bases of the double helix formed according to the pairing mentioned below; the bases C and G are capable of forming hydrogen bonds with the guanine of the G.C doublets; the base U is capable of forming hydrogen bonds with the adenine of the A.T or A.U doublets.

Figure 1A:
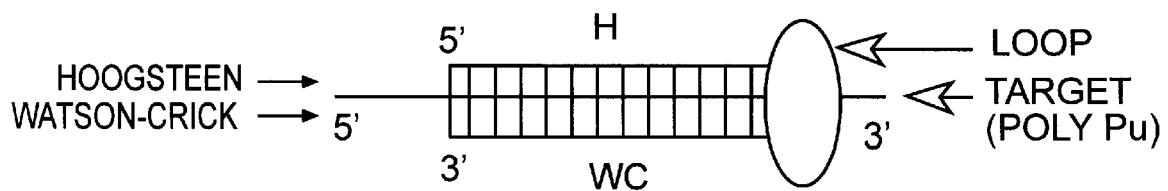
FIGS. 1a–1c depict embodiments of the triplex forming RNA oligonucleotides of the invention.
Figure 1B:
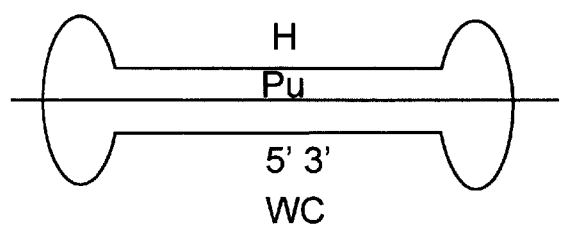
Figure 1C:
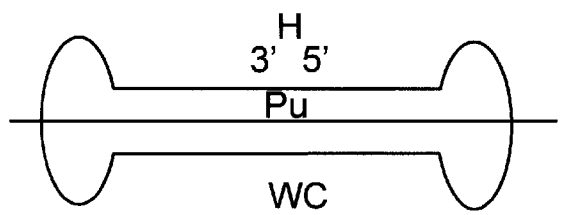

In this embodiment the therapeutic RNA of the invention forms a loop around the target nucleic acid or a portion of the latter, according to the configuration shown in FIG. 1a.

When the target nucleic acid (or a specific region of the latter) is composed essentially of pyrimidine bases (polyPy), the therapeutic RNA of the invention may include a first region composed of complementary purine bases (Watson-Crick region), one or two oligonucleotide arms, and a second region (Hoogsteen region) composed of the bases U and G or A and G, which interact with the purine bases of the double helix formed according to the pairing mentioned below; the base G is capable of forming hydrogen bonds (reverse Hoogsteen) with the guanine of the G.C doublets; the bases U and A are capable of forming hydrogen bonds with the adenine of the A.T or A.U doublets.

Figure 2:
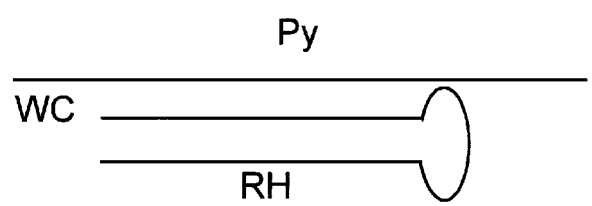
FIG. 2 depicts an embodiment of the triplex forming RNA oligonucleotides of the invention.

In this embodiment the therapeutic RNA of the invention forms a loop parallel to the target nucleic acid, according to the configuration shown in FIG. 2.

When the target nucleic acid (or a specific region of the latter) is composed essentially of bases T/U,C or T/U,G the therapeutic RNA of the invention may include a first region composed of complementary purine bases (Watson-Crick region), one or two oligonucleotide arms, and a second region composed of complementary pyrimidine bases of the purine bases (also Watson-Crick region), the 2 regions of the therapeutic RNA forming a Watson-Crick double helix whose purine strand interacts with the target nucleic acid, by forming Hoogsteen or reverse Hoogsteen bonds.

In this embodiment the therapeutic RNA of the invention forms a loop parallel to the target nucleic acid, according to the configuration shown in FIG. 5.

It is to be understood that, depending on the chosen single-strand target nucleic acid composition, a person skilled in the art can define other double-strand DNA sequences of the invention, which are based on the pairing of the Watson-Crick doublets and Hoogsteen or reverse Hoogsteen.

The arms(s) connecting the 2 regions of the therapeutic RNAs of the invention are oligonucleotide sequences which may contain any base of which the RNAs are composed (A, U, G or C). The sequence of the arm preferably must not be capable itself of pairing with the targeted nucleic acid, so as not to perturb the formation of the local triple helix. The length of this arm may be adapted by a person skilled in the art as a function of the targeted nucleic acid. It generally comprises between 3 and 6 bases, preferably between 3 and 5.

Figure 3A:
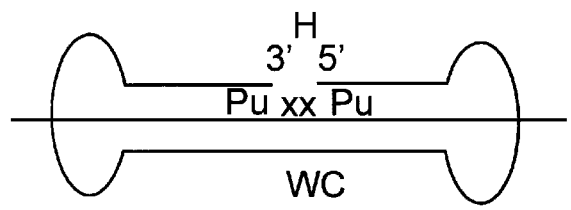
FIGS. 3a and 3b depict embodiments of the triplex forming RNA oligonucleotides of the invention.
Figure 3B:
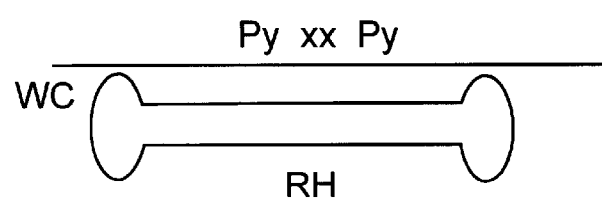
Figure 4A:
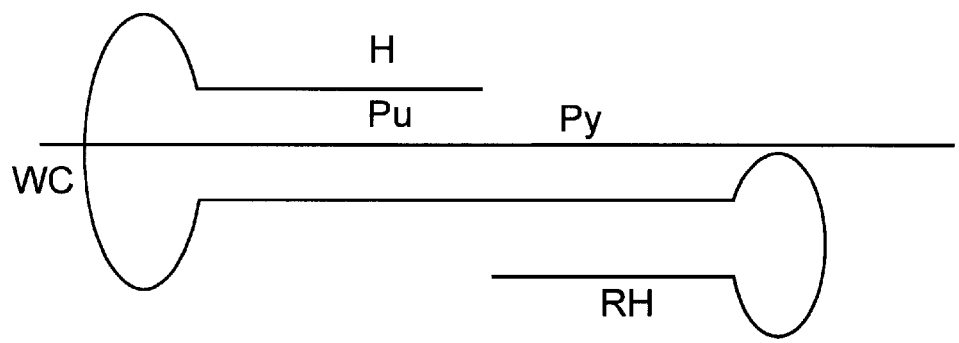
FIGS. 4a and 4b depict embodiments of the triplex forming RNA oligonucleotides of the invention.
Figure 4B:
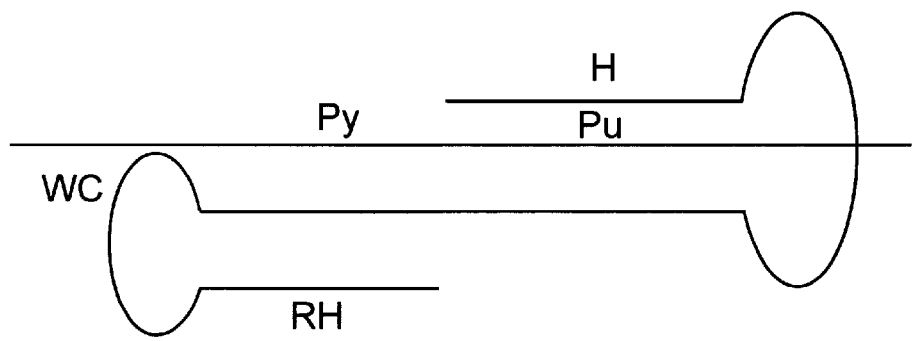

Furthermore, in a particular embodiment, the double stranded DNAs of the invention may code for composite RNAs including two oligonucleotide arms permitting the formation of two loops around and/or parallel to the single-strand targeted nucleic acid. Such composite RNAs have particularly advantageous properties:

first of all, they make it possible to increase further the stability of the triple helix formed, as well as its therapeutic effectiveness, because of an even greater steric hindrance (cf. FIGS. 1b, 1c, 3 and 4);

they make it possible to target single-strand nucleic acids in the oligopurine or oligopyrimidine regions interrupted by pyrimidine or purine bases respectively, by interrupting the Hoogsteen or reverse Hoogsteen region (cf. FIGS. 3a and 3b). This therefore makes it possible to widen the field of application of these therapeutic RNAs to any type of region of a single-strand nucleic acid;

they also make it possible to target single-strand nucleic acids composed of a chain linking of an oligopurine region and of an oligopyrimidine region and vice versa (FIG. 4). This therefore also widens the field of application of the therapeutic RNAs of the invention.

In a particular embodiment of the invention the double stranded DNA therefore codes for a composite RNA including:

a first region capable of forming a double helix with the targeted single-strand nucleic acid or with a portion of the latter, a second region capable of forming a triple helix with the double helix thus formed or with a portion of the latter, and two arms connecting each of the two regions at their ends (FIGS. 1b, 1c, 3 and 4).

In this embodiment one of the two regions of the composite RNA (Watson-Crick (FIG. 1b), Hoogsteen (FIGS. 1c and 3a) or reverse Hoogsteen (FIG. 3b)) is interrupted, because it contains the initiation site of the transcription.

In another particular embodiment of the invention the double stranded DNA codes for a composite RNA including:

a first region capable of forming a double helix with an oligopurine region of the targeted single-strand nucleic acid, an arm, a second region capable of forming a triple helix with the double helix thus formed or with a portion of the latter, a third region, connected to the first, capable of forming a double helix with an oligopyrimidine region of the targeted single-strand nucleic acid, a second arm, and a fourth region, connected to the third, capable of forming a triple helix with the double helix thus formed or with a portion of the latter (FIG. 4).

The double stranded DNAs of the invention (and the coded composite RNAs) preferably have a length greater than 10 bases and, more preferably, greater than 15 bases. This length is adapted by a person skilled in the art as a function of the length of the single-strand targeted nucleic acid, so as to ensure the stability, the specificity and the selectivity of the therapeutic RNA. Furthermore, to improve the stability of the triple helix it may be advantageous to lengthen one of the regions of the composite RNA, preferably the region forming a double helix.

The double stranded DNA may be a synthetic or semisynthetic DNA. It may be obtained by any technique known to a person skilled in the art, and especially by means of nucleic acid synthesizers. The sequence of this DNA is determined as a function of the chosen cell target, as indicated above.

Advantageously, the double stranded DNA of the invention also contains signals permitting the transcription (the production) of the therapeutic RNAs of the invention in the target cells. These signals include sequences permitting the initiation of the transcription (promoters) and, optionally, signals permitting the termination of transcription (terminators), as well as signals permitting the stabilization of the RNAs (for example a polyA tail). These different signals may be constitutive or regulated. In particular, they may involve promoter sequences of eukaryotic or viral genes or synthetic promoters. For example, they may involve promoter sequences originating from the genome of the cell which it is desired to infect. Similarly, they may involve promoter sequences originating from the genome of a virus. In this connection it is possible to mention, for example, E1A, MLP, CMV, RSV, HIV promoters and the like. It may be particularly advantageous to control the production of the therapeutic RNA directed against a virus by the infection itself (for example by employing the LTR promoter of the HIV virus, specifically induced in the presence of the HIV TAT protein). Moreover, these expression sequences may be modified by addition of activating or regulating sequences or the like. Furthermore, when the double stranded DNA does not contain any expression sequences, it may be inserted into a vector, downstream of such a sequence. A particularly advantageous expression system consists of the use of transcription promoters controlled specifically by RNA polymerase III. RNA polymerase III is, in fact, responsible for the synthesis of small cytoplasmic or nuclear RNAs exhibiting a high stability and not translated into protein. These small RNAs are especially the tRNAs, the rRNAs or some viral RNAs such as especially the VA RNAs of adenovirus. According to an advantageous embodiment of the invention the double stranded DNA includes a promoter transcribed specifically by RNA polymerase III. More particularly the double stranded DNA can be inserted into a gene transcribed specifically by RNA polymerase III (FR 2,687,411) or fused downstream of such a gene (EP 387 775).

The present invention offers many advantages when compared with the previous techniques of control of the expression of genes. In particular, the in-vivo production of RNAs according to the invention which are capable of forming triple helices with single-strand cell nucleic acids makes it possible to increase the selectivity of the therapeutic molecules for their cell targets. The use of oligonucleotides as therapeutic agents requires, in fact, a specific and selective recognition of the cell target. Thus, for example in the case of ras the mRNA of the oncogene differs from that of the protooncogene only in a point mutation. In this case it is important that the oligonucleotide should inhibit the expression of the oncogene as effectively as possible without, however, affecting that of the protooncogene. It is therefore crucial to have highly discriminating therapeutic agents at one's disposal. In the case of conventional antisense, each base of the target sequence is recognized by only one base of the oligonucleotide sequence, and a single mispairing may have only a small influence on the formation and the stability of the double strand. However, in the case of the therapeutic molecules of the invention, a double recognition is necessary (each base in the target sequence is recognized by 2 bases of the therapeutic RNA), and this greatly enhances the discriminating power.

The therapeutic RNAs produced within the scope of the invention also have a better-therapeutic effectiveness than conventional antisense. In fact, the physical hindrance produced by the therapeutic molecules of the invention is greater than in the case of conventional antisense, since the former form a loop around the target, which is capable of resulting in the uncoupling of a reverse transcriptase or of a DNA polymerase, and are thus capable of interacting in the translation of the mRNA into protein, with the ribosome in elongation, the enzymes and/or other factors involved.

Furthermore, because of the formation of a triple helix (Watson-Crick and Hoogsteen or reverse Hoogsteen bonds), the molecules of the invention form more stable complexes with the targeted nucleic acids than conventional antisense. This property further reinforces the advantages of the molecules of the invention, which therefore constitute particularly powerful therapeutic agents.

Finally, the possibility of generating the therapeutic molecules according to the invention in vivo makes it possible to produce these therapeutic molecules at high levels starting with a single double stranded DNA (or a vector containing it) introduced into the target cell. Moreover, it makes it possible to generate these molecules directly in the desired cell compartments of the target cell.

The double stranded DNA according to the invention may be employed as it is, for example after injection into man or animal, to control the expression of a given gene. In particular, it can be injected in the form of naked DNA using the technique described in application WO 90/11092. It may also be administered in complexed form, for example with DFAE-dextran (Pagano et al., J.Virol. 1.(1967) 891), with nuclear proteins (Kaneda et al., Science 243 (1989) 375) or with lipids (Felgner et al., PNAS 84 (1987) 7413). It can also be incorporated into a vector such as a liposome (Fraley et al., J.Biol. Chem. 255 (1980) 10431) or a nanoparticle. Liposomes are phospholipid vesicles containing an internal aqueous phase in which the nucleic acids can be encapsulated. The synthesis of liposomes and their use for the transfer of nucleic acids is known in the prior art (WO91/06309, WO92/19752, WO92/19730). Nanoparticles are particles of small size, generally smaller than 500 nm, capable of conveying or vectorizing an active principle (such as a nucleic acid) into cells or into blood circulation. The nanoparticles may consist of polymers containing a majority of degradable units such as polylactic acid, optionally copolymerized with polyethylene glycol. Other polymers usable in the production of nanoparticles have been described in the prior art (see, for example EP 275 796; EP 520 889).

The double stranded DNA of the present invention preferably forms part of a vector. The use of such a vector makes it possible, in fact, to improve the effectiveness of transfer of the double stranded DNA into the target cells, and also to increase its stability in the said cells, and this makes it possible to obtain a lasting therapeutic effect. Furthermore, the use of vectors also makes it possible to target some cell populations in which the therapeutic molecules must be produced. Moreover, it is possible to introduce a number of double stranded DNAs into the same vector, and this also increases the effectiveness of the treatment.

Another subject of the invention therefore relates to a vector including a double stranded DNA coding for an RNA capable of forming a triple helix with a single-strand targeted nucleic acid.

The vector employed may be from various sources, so long as it is capable of transforming animal cells, preferably human cells. It may equally well involve a plasmid or viral vector. In a preferred embodiment of the invention a viral vector is employed, which may be chosen from adenoviruses, retroviruses, adeno-associated viruses (AAV), the herpes virus, cytomegalovirus, vaccinia virus and the like.

In this respect, another subject of the present invention is any recombinant virus including, inserted into its genome, a double stranded DNA coding for an RNA capable of forming a triple helix with a single-strand target nucleic acid.

Vectors derived from adenoviruses, retroviruses or AAVs incorporating heterologous nucleic acid sequences have been described in the literature [Akli et al., Nature Genetics 3 (1993) 224; Stratford-Perricaudet et al., Human Gene Therapy 1 (1990) 241; EP 185 573, Levrero et al., Gene 101 (1991) 195; Le Gal la Salle et al., Science 259 (1993) 988; Roemer and Friedmann, Eur. J. Biochem. 208 (1992) 211; Dobson et al., Neuron 5 (1990) 353; Chiocca et al., New Biol. 2 (1990) 739; Miyanohara et al., New Biol. 4 (1992) 238; WO91/18088].

Advantageously, the recombinant virus according to the invention is a defective virus. The term "defective virus" denotes a virus incapable of replicating in the target cell. In general, the genome of the defective viruses employed within the scope of the present invention is therefore devoid at least of the sequences necessary for the replication of the said virus in the infected cell. These regions may be either removed (wholly or partially) or made nonfunctional, or substituted by other sequences and especially by the sequence of the double stranded nucleic acid of the invention. Nevertheless, the defective virus preferably retains the sequences of its genome, which are necessary for the encapsidation of the virus particles.

It is particularly advantageous to employ the nucleic sequences of the invention in a form incorporated into a defective recombinant adenovirus.

Actually, different adenovirus serotypes exist, whose structure and properties vary somewhat, but which are not pathogenic to man, and especially to individuals who are not immunodepressed. Furthermore, these viruses do not become integrated into the genome of the cells which they infect and may incorporate large fragments of exogenous DNA. Among the various serotypes it is preferable within the scope of the present invention to employ the adenoviruses of type 2 or 5 (Ad 2 or Ad 5). In the case of adenoviruses Ad 5 the sequences necessary for the replication are the E1A and E1B regions. As indicated above, it is very particularly advantageous to employ a defective recombinant adenovirus including a double stranded DNA of the invention, inserted into a VA gene.

Furthermore, the small size of the double stranded DNAs of the invention makes it advantageously possible to incorporate simultaneously in the same vector a number of these DNAS, which are identical (directed against the same target nucleic acid) or different (directed against different target nucleic acids). A particular embodiment of the invention therefore consists of a vector, especially viral, including at least two double stranded DNAs as defined above.

The defective recombinant viruses of the invention may be prepared by homologous recombination between a defective virus and a plasmid bearing, inter alia, the double stranded DNA as defined above (Levrero et al., Gene 101 (1991) 195; Graham, EMBO J. 3(12) (1984) 2917). The homologous recombination takes place after cotransfection of the said virus and plasmid to an appropriate cell line. The cell line employed must preferably (i) be transformable by the said components and (ii) comprise sequences capable of complementing the part of the genome of the defective virus, preferably in integrated form to avoid the risks of recombination. By way of example of line usable for the preparation of adenoviruses or of recombinant AAVs which are defective it is possible to mention the human embryo kidney line 293 (Graham et al., J. Gen. Virol. 36 (1977) 59) which contains especially, integrated into its genome, the left-hand part of the genome of an adenovirus Ad5 (12%). By way of example of line usable for the preparation of defective recombinant retroviruses it is possible to mention the line CRIP (Danos and Mulligan, PNAS 85 (1988) 6460).

The viruses which have reproduced are subsequently recovered and purified according to the classical techniques of molecular biology.

Another subject of the present invention is a pharmaceutical composition including at least one vector or a double stranded DNA as defined above.

The pharmaceutical compositions of the invention may be formulated with a view to administration by a topical, oral, parenteral, intranasal, intravenous, intramuscular, subcutaneous, intraocular or other route.

The pharmaceutical compositions preferably contain pharmaceutically acceptable carriers for an injectable formulation. These may be in particular saline solutions (monosodium or disodium phosphate, sodium, potassium, calcium or magnesium chloride and the like or mixtures of such salts), which are sterile and/or isotonic, or dry, especially freeze-dried compositions which make it possible to form injectable solutions by addition, depending on the circumstances, of sterilized water or of physiological saline.

The DNA (or vector) doses employed for the administration can be adapted as a function of various parameters, and especially as a function of the method of administration employed, of the pathology involved, of the nucleic acid to be expressed, or else of the required duration of treatment. In general, with regard to the recombinant viruses according to the invention, these are formulated and administered in the form of doses of between $10^4$ and $10^{14}$ pfu/ml, and preferably $10^6$ to $10^{10}$ pfu/ml. The term pfu (plaque forming unit) corresponds to the infective power of a virus solution, and is determined by infection of an appropriate cell culture and measuring, generally after 48 hours, the number of areas of infected cells. Techniques for determining the pfu content of a virus solution are well documented in the literature.

Such pharmaceutical compositions can be employed in man, for the treatment and/or the prevention of diseases resulting from an abnormal expression of genes (overexpression of a cell gene, expression of a mutated gene and the like), or of viral diseases (HIV, herpes, hepatitis and the like).

Another subject of the present invention is a process for controlling the expression of genes in a specific cell, including the introduction into the said cell of a double stranded DNA as defined above. This DNA may be administered as it is or as described above, after it has been incorporated into a vector. This process of the invention is very particularly usable in the context of a cell therapy, for modifying ex vivo the expression of genes in specific cell populations taken from an organism and before they are readministered. This may involve a gene whose expression levels are modified in the pathology in question (e.g. oncogene, viral gene), or a gene whose expression level is not affected but takes part in the development of the said pathology (regulator gene, GAP or GRF gene and the like).

Another subject of the present invention is a process for controlling the expression of genes in vivo, including the administration of a pharmaceutical composition as defined above.

A further subject of the present invention is a method for the treatment of diseases resulting from an abnormal expression of genes, including the administration of a pharmaceutical composition as defined above, including a double stranded DNA coding for an RNA capable of modifying the expression of the said genes.

The present invention will be described more fully with the aid of the examples which follow, which must be considered as illustrative and not implying any limitation.
General Cloning Techniques The methods classically employed in molecular biology, such as the preparative extractions of plasmid DNA, the centrifuging of plasmid DNA in caesium chloride gradient, electrophoresis on agar or acrylamide gels, purification of DNA fragments by electroelution, extraction of proteins with phenol or with phenol-chloroform, precipitation of DNA in saline medium with ethanol or isopropanol, transformation in Escherichia coli, and the like, are well known to a person skilled in the art and are widely described in literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

The plasmids of pBR322, pUC and pSP65 type and the phages of the M13 series are from a commercial source (Bethesda Research Laboratories, Promega).

For ligations, the DNA fragments may be separated according to their size by electrophoresis on agarose or acrylamide gels, extracted with phenol or with a phenol/chloroform mixture, precipitated with ethanol and then incubated in the presence of DNA ligase of phage T4 (Biolabs) according to the supplier's recommendations.

Filling of the prominent 5' ends may be performed using the Klenow fragment of DNA polymerase I of *E. coli* (Biolabs) according to the supplier's specifications. Destruction of the prominent 3' ends is performed in the presence of DNA polymerase of phage T4 (Biolabs) employed according to the manufacturer's recommendations. Destruction of the prominent 5' ends is performed by a controlled treatment with nuclease S1.

The directed in-vitro mutagenesis using synthetic oligodeoxynucleotides may be performed according to the method developed by Taylor et al. [Nucleic Acids Res. 13 (1985) 8749–8764] using the kit distributed by Amersham.

The enzymatic amplification of DNA fragments by the so-called PCR technique [Polymerase-catalyzed Chain Reaction, Saiki R. K. et al., Science 230 (1985) 1350–1354; Mullis K. B. et Faloona F. A., Meth. Enzym. 155 (1987) 335–350] may be performed by employing a "DNA thermal cycler" (Perkin Elmer Cetus) according to the manufacturer's specifications.

The verification of the nucleotide sequences may be performed by the method developed by Sanger et al. [Proc. Natl. Acad. Sci. USA, 74 (1977) 5463–5467] using the kit distributed by Amersham.

EXAMPLES

Example 1

Synthesis of Double Stranded DNA Coding for Triple-helix RNAs Directed against the Polypurine Tract Sequence of the HIV Virus.

This example describes the synthesis of various double stranded DNAs coding for triple-helix RNAs directed against a sequence present twice in the genome of the HIV virus (BRUCG). This sequence is located between the residues 4369–4382 and 8662–8677. This sequence, known as Polypurine Tract or PPT, plays an essential part in the initiation of the synthesis of the + strand of DNA. The formation of a triple helix in this region should result in a particularly effective inhibition of polymerase activity and should thus prevent the production of proviral DNA.

The Polypurine Tract region of the HIV virus includes 16 purine bases, the sequence of which is given in SEQ ID No.1.

Various double stranded DNAs coding for triple-helix RNAs according to the invention, directed against this target, have been synthesized. The synthesis has been carried out by means of an automatic nucleotide synthesizer, employing the phosphoramidite chemistry according to the technique described by Giovannangeli et al. (J. Am. Chem. Soc. 113 (1991) 7775). The sequence of these DNAs is given in the table below.

| PPT TARGET SEQ ID No. 1 | 5'-CCACTTTTT 8662 2nd region | AAAAGAAAAGGGGGGA Arm | CTGG-3' 8677 1st region |
|---|---|---|---|
| DNA db | 5' | | 3' |
| SEQ ID No. 2 | TTTTCTTTTCCCCCCT | TTTTT | TCCCCCCTTTTCTTTTAA |
| SEQ ID No. 3 | TTTTCTTTTCCCCCCT | TTTT | TCCCCCCTTTTCTTTTAA |
| SEQ ID No. 4 | TTTTCTTTTCCCCCCT | TTT | GTCCCCCCTTTTCTTTTAA |
| SEQ ID No. 5 | TTTCCCCCCT | TCT | GTCCCCCCTTTT |
| SEQ ID No. 6 | TTTGGGGGGT | TCT | GTCCCCCCTTTT |
| SEQ ID No. 7 | TTTTCTTTTCCCCCCT | TCT | GTCCCCCCTTTTCTTTT |
| SEQ ID No. 8 | TTTTCTTTTGGGGGGT | TCT | GTCCCCCCTTTTCTTTT |

Example 2

Synthesis of a Double Stranded DNA Coding for Triple-helix RNAs Directed Against the Gag Gene of the HIV Virus.

This example describes the synthesis of various double stranded DNAs coding for triple-helix RNAs directed against the gag gene of the HIV virus, in the regions included, on the one hand, between the residues 324 and 336 (SEQ ID No.9) and, on the other hand, between the residues 404 and 419 (SEQ ID No.12). The gag gene codes for structural proteins of the HIV virus (MAp17, CAp24 and NCp15) and is therefore essential for the encapsidation and the production of the virus particles.

The 2 regions of the gag gene of the HIV virus which are identified above include 13 and 16 purine bases respectively.

Various double stranded DNAs coding for the triple-helix RNAs according to the invention, directed against these targets, have been synthesized. The synthesis has been carried out by means of an automatic nucleotide synthesizer, using the phosphoramidite chemistry according to the technique described by Giovannangeli et al. (J. Am. Chem. Soc. 113 (1991) 7775). The sequence of these DNAs is given in the table below.

presence of a plasmid including a part of the gag gene of the HIV virus (which contains the sequences SEQ ID Nos.9 and 12) under the control of the promoter T7 (for the DNAs of sequence SEQ ID Nos.10–11 and 13–15). These experiments make it possible to follow the effect of the therapeutic RNAs of the invention on the transcription of the int and gag genes respectively by the polymerase RNAs SP6 and T7, and on the production of the corresponding proteins (that is to say the translation of the RNAs).

3.3. In-vivo measurement of the replication rate of the HIV virus in the presence or in the absence of the double stranded DNAs of the invention. For this purpose, for example, the double stranded DNAs of the invention are introduced into growing T lymphocytes and the coded RNAs are expressed (in a stable or transient manner). The lymphocytes are then infected with the HIV virus and the rate of replication of the virus is evaluated by determining the antigen p24.

```
GAG TARGET   5'-GCT AGAAGGAGAGAGA TGGG-3'
SEQ ID No.9         324          336
DNA db          2nd region            Arm    1st region
                5'                                      3'
SEQ ID No. 10 TCTTCCTCTCTCT          TATT   TCTCTCTCCTTCTTTT
SEQ ID No. 11 TGTTGGTGTGTGT          TATT   TCTCTCTCCTTCTTTT
GAG TARGET   5'-GCC AGGGGGAAAGAAAAAA TAT-3'
SEQ ID No. 12       404              419
SEQ ID No. 13 TCCCCCTTTCTTTTTT       CTCC   TTTTTTCTTTC-
                                            CCCCTTTT
SEQ ID No. 14 TCCCCCTTTCTTT          CTCC      TTTCTTTC-
                                            CCCCTTTT
SEQ ID No. 15 TGGGGGTTTGTTT          CTCC      TTTCTTTC-
                                            CCCCTTTT
```

Example 3
Inhibition of the Infection Cycle of the HIV by the Double Stranded DNAs of the Invention.

The functionality of the double stranded DNAs of the invention which are described in Examples 1 and 2 is demonstrated by experiments of various types and especially by physicochemical studies, by transcription, reverse transcription or translation experiments in vitro and by measuring the effect on virus replication.

3.1. The physicochemical study of the interaction between the targeted nucleic acid and the therapeutic RNA of the invention makes it possible to obtain thermodynamic and kinetic characteristics of the complex formed. For this purpose the double stranded DNAs synthesized above or the therapeutic RNAs are incubated in the presence of the targeted nucleic acid and then the complex originating from this reaction is analysed by absorption spectroscopy and by retardation experiments on gel. These various studies show how each of the therapeutic RNAs is capable of interacting with its respective target.

3.2. Measurement of the effect of the therapeutic RNA on the transcription, the translation and the reverse transcription of a gene containing the target sequence, placed under the control of a promoter (SP6, T7 or T3). These in-vitro experiments make it possible to measure directly the effect of the RNAs of the invention on each stage of the viral cycle. More precisely, the double stranded DNAs described above or the composite RNAs for which they code are incubated in a reaction medium including the constituents and the enzymes necessary for the transcription and/or for the translation, either in the presence of a plasmid including the gene of the integrase of the HIV virus (which contains the sequence SEQ ID No.1) under the control of the promoter SP6 (for the DNAs of sequence SEQ ID Nos.2–8), or in the Example 4

Synthesis of Double Stranded DNA Coding for Triple-helix RNAs Directed Against the IGF-I Gene (Insulin-like Growth Factor I).

This example describes the synthesis of various double stranded DNAs coding for triple-helix RNAs directed against the IGF-I gene, in a region included between the residues 40 and 62 (SEQ ID No.16).

This region of the IGF-I gene, identified above, includes 23 purine bases and is located in the transcribed but not translated 5' part of the gene.

Various double stranded DNAs coding for triple-helix RNAs according to the invention, directed against this target, have been synthesized. The synthesis was carried out by means of an automatic nucleotide synthesizer by employing the phosphoramidite chemistry according to the technique described by Giovannangeli et al., (J. Am. Chem. Soc. 113 (1991) 7775). The sequence of these DNAs is given in the table below.

```
IGF-I   5'- AGAAGAGGGAGAGAGAGAGAGAAGG...-3'
TARGET      40                         62
SEQ ID
NO. 16
DNA db      2nd region         Arm    1st region
            5'                                      3'
SEQ ID  TCTTCTCCC(TC)5TTCC    TCCG    CCTT(CT)5CCCTCTTCT
No. 17
```

What is claimed is:

1. A recombinant vector, wherein the vector comprises a double stranded DNA sequence coding for an RNA which forms a triple helix with a single-stranded target nucleic acid, and signals permitting the transcription of the RNA in a target cell.

2. The vector according to claim 1, wherein the encoded RNA comprises:
   (a) a first region which forms a double helix with the single-stranded target nucleic acid, and
   (b) a second region which forms a triple helix with the double helix thus formed.

3. The vector according to claim 2, wherein the first region of the RNA forms a double helix by interaction of Watson-Crick type with the targeted single-stranded nucleic acid and then the second region forms a triple helix with this double helix by hydrogen bonds.

4. The vector according to claim 2, wherein the encoded RNA further comprises an oligonucleotide arm of from 3 to 6 bases between the first and second regions.

5. The vector according to claim 2, wherein the two regions of the encoded RNA are interrupted, and wherein the encoded RNA further comprises an oligonucleotide arm connecting the two regions.

6. The vector according to claim 1, wherein the RNA comprises first and second regions which forms a double helix with each other, and thereafter forming a triple helix with the single stranded target nucleic acid.

7. The vector according to claim 6, wherein the two regions of the RNA form the double helix by pairing of Watson-Crick type, and this double helix interacts with the single-stranded target nucleic acid by hydrogen bonds.

8. The vector according to claim 1, wherein the RNA comprises:
   (a) a first region which forms a double helix with an oligopurine region of the single-stranded target nucleic acid,
   (b) a second region which forms a triple helix with the double helix formed between the first region and the oligopurine region of the single stranded target nucleic acid,
   (c) a first oligonucleotide arm connecting the first and second regions,
   (d) a third region which forms a double helix with an oligopyrimidine region of the single-stranded target nucleic acid,
   (e) a fourth region which forms a triple helix with the double helix formed between the third region and the oligopyrimidine region of the single-stranded target nucleic acid, and
   (f) a second oligonucleotide arm connecting the third and fourth region.

9. The vector according to claim 1, wherein the transcription signals are constitutive.

10. The vector according to claim 1, wherein the transcription signals are regulated.

11. The vector according to claim 1, wherein the transcription signal is a promoter controlled specifically by RNA polymerase III.

12. The vector according to claim 1, wherein the double stranded DNA sequence is selected from the group consisting of SEQ ID Nos. 2, 3, 4, 5, 6, 7, 8, 10, 11, 13, 14, 15 and 17.

13. The vector according to claim 1, which is a replication defective virus.

14. The vector according to claim 13, wherein the virus is selected from the group consisting of adenovirus, adeno-associated virus, herpes virus, cytomegalovirus and vaccinia virus.

15. The vector according to claim 14, wherein the virus is a defective adenovirus.

16. A recombinant viral vector selected from the group consisting of adenovirus, adeno-associated virus, herpes virus, cytomegalovirus and vaccinia virus, wherein the viral vector comprises more than one double stranded DNA sequence coding for an RNA which forms a triple helix with a single-stranded target nucleic acid, and signals permitting the transcription of the RNAs in a target cell.

17. The vector according to claim 16, wherein each of the double-stranded DNA sequences encodes a different RNA which forms a triple helix with the single-stranded target nucleic acid.

18. A composition comprising a vector according to claim 1, wherein said vector is complexed with DEAE-dextran, nuclear proteins, or lipids.

19. A composition comprising a vector according to claim 1, wherein said vector is incorporated into liposomes or nanoparticles.

20. An RNA comprising:
(a) a first region which forms a double helix with an oligopurine region of a single-stranded target nucleic acid,
(b) a second region which forms a triple helix with the double helix formed between the first region and the oligopurine region of the single stranded target nucleic acid,
(c) a first oligonucleotide arm connecting the first and second regions,
(d) a third region which forms a double helix with an oligopyrimidine region of the single-stranded target nucleic acid,
(e) a fourth region which forms a triple helix with the double helix formed between the third region and the oligopyrimidine region of the single-stranded target nucleic acid, and
(f) a second oligonucleotide arm connecting the third and fourth region, wherein two triple helices are formed.

* * * * *